(12) United States Patent
Rao et al.

(10) Patent No.: US 8,288,597 B2
(45) Date of Patent: Oct. 16, 2012

(54) DEHYDROFLUORINATION PROCESS TO MANUFACTURE HYDROFLUOROOLEFINS

(75) Inventors: Velliyur Nott Mallikarjuna Rao, Wilmington, DE (US); Allen Capron Sievert, Elkton, MD (US); Mario Joseph Nappa, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 515 days.

(21) Appl. No.: 12/440,062

(22) PCT Filed: Sep. 5, 2007

(86) PCT No.: PCT/US2007/019314
§ 371 (c)(1),
(2), (4) Date: Mar. 25, 2009

(87) PCT Pub. No.: WO2008/030439
PCT Pub. Date: Mar. 13, 2008

(65) Prior Publication Data
US 2010/0121115 A1    May 13, 2010

Related U.S. Application Data

(60) Provisional application No. 60/842,425, filed on Sep. 5, 2006.

(51) Int. Cl.
*C07C 17/00* (2006.01)

(52) U.S. Cl. .......................... 570/156; 570/155; 570/157
(58) Field of Classification Search .................. 570/155, 570/156, 157
See application file for complete search history.

(56) References Cited

U.S. PATENT DOCUMENTS

| 4,560,759 A | 12/1985 | Hiratani | |
| 2003/0060670 A1* | 3/2003 | Nair et al. | 570/155 |

FOREIGN PATENT DOCUMENTS

| JP | 11292807 | 10/1999 |
| WO | 03027051 A1 | 4/2003 |

OTHER PUBLICATIONS

CRC Handbook of Chemistry and Physics, 81st Edition, (2000-2001), Book Not Included.
I. L. Knunyants et al., Reactions of Fluoro Olefins Communication 13. Catalytic Hydrogenation of Perfluoro Olefins, Bulletin of the Academy of Sciences of the USSR, Division of Chemical Sciences, 1960, p. 1312-1317, XP000578879.

* cited by examiner

*Primary Examiner* — Jafar Parsa

(57) ABSTRACT

Disclosed is a process for the manufacture of hydrofluoroolefins of the structure $CF_3CF=CHY$, wherein Y can be H or F, comprising reacting at least one fluoropropane reactant of the structure $CF_3CFXCFYH$, wherein X can be either F or H, and Y can be either F or H, provided that both X and Y' are not both F, with a basic aqueous solution in the presence of a non-aqueous, non-alcoholic solvent, and in the presence of a phase transfer catalyst.

14 Claims, No Drawings

DEHYDROFLUORINATION PROCESS TO MANUFACTURE HYDROFLUOROOLEFINS

BACKGROUND INFORMATION

1. Field of the Disclosure

This disclosure relates in general to processes for the production of fluorinated olefins.

2. Description of the Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, HFC-134a being the most widely used at this time, have zero ozone depletion potential and thus are not affected by the current regulatory phase-out as a result of the Montreal Protocol.

In addition to ozone depleting concerns, global warming is another environmental concern. Thus, there is a need for heat transfer compositions that have not only low ozone depletion potentials, but also low global warming potentials. Certain hydrofluoroolefins meet both goals. Thus there is a need for manufacturing processes that provide halogenated hydrocarbons and fluoroolefins that contain no chlorine and also have lower global warming potential than current commercial refrigeration products.

DESCRIPTION OF THE INVENTION

The description below is exemplary and explanatory only and is not restrictive of the invention, as defined in the appended claims. Other features and benefits of any one or more of the embodiments will be apparent from the following detailed description, and from the claims.

Group numbers corresponding to columns within the Periodic Table of the elements use the "New Notation" convention as seen in the *CRC Handbook of Chemistry and Physics*, 81$^{st}$ Edition (2000-2001).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise. Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Disclosed is a process for the manufacture of hydrofluoroolefins of the structure $CF_3CF=CHY$, wherein Y can be H or F, comprising reacting at least one fluoropropane reactant of the structure $CF_3CFXCFY'H$, wherein X can be either F or H, and Y' can be either F or H, provided that both X and Y' are not both F, with a basic aqueous solution in the presence of a nonaqueous, nonalcoholic solvent, and in the presence of a phase transfer catalyst.

In certain embodiments, the hydrofluoroolefin produced by the disclosed embodiments are 1,2,3,3,3-pentafluoro-1-propene (HFC-1225ye) (both isomers) and 2,3,3,3-tetrafluoro-1-propene (HFC-1234yf), each having zero ozone depletion and low global warming potential and have been identified as potential refrigerants.

As used herein, the basic aqueous solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid medium in the basic aqueous solution is at least 90% water. In one embodiment the water is tap water; in other embodiments the water is deionized or distilled.

The base in the aqueous basic solution is selected from the group consisting of hydroxide, oxide, carbonate, or phosphate salts of alkali, alkaline earth metals and mixtures thereof. In one embodiment, bases which may be used lithium hydroxide, sodium hydroxide, potassium hydroxide, calcium hydroxide, magnesium oxide, calcium oxide, sodium carbonate, potassium carbonate, sodium phosphate, potassium phosphate, or mixtures thereof.

In certain embodiments, the non-aqueous non-alcoholic solvent is selected from the group consisting of alkyl and aryl nitriles, alkyl and aryl ethers, amides, ketones, sulfoxides, phosphate esters and mixtures thereof.

Said alkyl groups may be cyclic or acyclic and straight-chain or branched alkyl groups. In another embodiment, the solvent is selected from the group consisting of acetonitrile, propionitrile, butyronitrile, methyl glutaronitrile, adiponitrile, benzonitrile, ethylene carbonate, propylene carbonate, methyl ethyl ketone, methyl isoamyl ketone, diisobutyl ketone, anisole, 2-methyltetrahydrofuran, tetrahydrofuran, dioxane, diglyme, triglyme, tetraglyme, N,N-dimethyl formamide, N,N-dimethyl acetamide, N-methylpyrrolidinone, sulfolane, dimethyl sulfoxide, perfluoro-N-methyl morpholine, perfluorotetrahydrofuran, and mixtures thereof. Preferred solvents include acetonitrile, adiponitrile, 2-methyl tetrahydrofuran, tetrahydrofuran, dioxane, diglyme, and tetraglyme.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrofluorination reaction.

The phase transfer catalyst is selected from the group consisting of crown ethers, onium salts, cryptands, polyalkylene glycols, and mixture thereof.

As used herein, cryptands are any of a family of bi- and polycyclic multidentate ligands for a variety of cations.

In one embodiment, the process is for the manufacture of 1,2,3,3,3-pentafluoro-1-propene (HFC-1225ye) by dehydrofluorination of 1,1,1,2,2,3-hexafluoropropane (HFC-236cb). HFC-1225ye may exist as two configurational isomers, E, or Z. HFC-1225ye as used herein refers to the isomers, E-HFC-1225ye (CAS RN 5595-10-8) or Z-HFC-1225ye (CAS RN 5528-43-8), as well as any combinations or mixtures of such isomers.

In another embodiment, the process is for the manufacture of 1,2,3,3,3-pentafluoro-1-propene (HFC-1225ye) by dehydrofluorination of 1,1,1,2,3,3-hexafluoropropane (HFC-236ea). In yet another embodiment, the process for the manufacture of 2,3,3,3-tetrafluoro-1-propene (HFC-1234yf) from 1,1,1,2,3-pentafluoropropane (HFC-245eb) is provided. As used herein, the term fluoropropane encompasses each of 1,1,1,2,2,3-hexafluoropropane, 1,1,1,2,3,3-hexafluoropropane and 1,1,1,2,3-pentafluoropropane.

In one embodiment, the fluoropropane is 1,1,1,2,2,3-hexafluoropropane (HFC-236cb) which can be produced by many known methods in the art. For example, HFC-236cb can be prepared by reaction of tetrafluoroethylene with difluoromethane in the presence of a Lewis acid catalyst. In another embodiment, the fluoropropane is 1,1,1,2,3,3-hexafluoropropane (HFC236ea) which can be produced by many known methods in the art. For example, HFC-236ea can be prepared by hydrogenation of readily available hexafluoropropylene.

In one embodiment, the dehydrofluorination of fluoropropane is accomplished using a basic aqueous solution in the presence of a non-aqueous, non-alcoholic solvent in which the fluoropropane is at least partially miscible. In one embodiment, the base in the basic aqueous solution includes alkali metal or alkaline earth metal hydroxides and oxides, or mixtures thereof, which can include without limitation lithium hydroxide, sodium hydroxide, potassium hydroxide, calcium hydroxide, magnesium oxide, calcium oxide, sodium carbonate, potassium carbonate, sodium phosphate, potassium phosphate, or mixtures thereof.

The amount of base (in the basic aqueous solution) required to convert a fluoropropane to a hydrofluoroolefin is approximately the stoichiometric quantity or about 1 mole of base to one mole of fluoropropane. In one embodiment, it may be desirable (e.g., to increase reaction rate) to employ a ratio of base to fluoropropane of greater than one. In some embodiments, large excesses of base (in the basic aqueous solution) are to be avoided as further reaction of the desired hydrofluoroolefin may occur. Thus, in some embodiments, it may be necessary to employ an amount of base (in the basic aqueous solution) that is slightly below the stoichiometric so as to minimize secondary reactions. Thus, in one embodiment, the molar ratio of base (in the basic aqueous solution) to fluoropropane is from about 0.75:1 to about 10:1. In another embodiment, the molar ratio of base (in the basic aqueous solution) to fluoropropane is from about 0.9:1 to about 5:1. In yet another embodiment, the molar ratio of base to fluoropropane is from about 1:1 to about 4:1.

In one embodiment, the dehydrofluorination is conducted within a temperature range at which the fluoropropane will dehydrofluorinate. In one embodiment, such temperatures can be from about 20° C. to about 150° C. In another embodiment, the reaction is conducted in the range of from about 30° C. to about 110° C. In yet another embodiment, the reaction is carried out in the range of from about 40° C. to about 90° C.

The reaction pressure is not critical. The reaction can be conducted at atmospheric pressure, super-atmospheric pressure, or under reduced pressure. In one embodiment, the reaction is carried out at atmospheric pressure.

In one embodiment, a solid base (e.g., KOH, NaOH, LiOH or mixtures thereof) is dissolved in water, or alternatively, a concentrated solution of a base (e.g., 50% by weight aqueous potassium hydroxide) is diluted to the desired concentration with water. The non-aqueous, non-alcoholic solvent for the method is then added with agitation under otherwise ambient conditions. In one embodiment, a solvent for the reaction can be a nitrile, ether, amide, ketone, sulfoxide, phosphate ester, or mixtures thereof. In another embodiment, the solvent is selected from the group consisting of acetonitrile, adiponitrile, 2-methyltetrahydrofuran, tetrahydrofuran, dioxane, diglyme, tetraglyme, perfluorotetrahydrofuran, and mixtures thereof.

In one embodiment, the base need not be highly soluble in the solvent. An amount of a phase transfer catalyst may be added to the solvent for the reaction in quantities that improve the solubility of the base therein. In one embodiment, the amount of phase transfer catalyst used will be from about 0.001 to about 10 mole percent based on the total amount of base present. In another embodiment, the amount of phase transfer catalyst used will be from about 0.01 to about 5 mole percent based on the total amount of base present. In yet another embodiment, the amount of phase transfer catalyst used will be from about 0.05 to about 5 mole percent based on the total amount of base present. In one embodiment of the invention, an aqueous or inorganic phase is present as a consequence of the base and an organic phase is present as a result of the fluoropropane and the non-aqueous, non-alcoholic solvent.

In some embodiments, the phase transfer catalyst can be ionic or neutral. In one embodiment, the phase transfer catalyst is selected from the group consisting of crown ethers, onium salts, cryptands and polyalkylene glycols and mixtures and derivatives thereof.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. In some embodiments, it is preferred to match crown ether phase transfer catalysts with certain bases used in the basic aqueous solutions. In one embodiment, crown ethers include 18-crown-6, is used in combination with potassium hydroxide basic aqueous solution; 15-crown-5, is used in combination with sodium hydroxide basic aqueous solution; 12-crown-4, is used in combination with lithium hydroxide basic aqueous solution. Derivatives of the above crown ethers are also useful, e.g., dibenzo-18-crown-6, dicyclohexano-18-crown-6, and dibenzo-24-crown-8 as well as 12-crown-4. Other polyethers particularly useful in combination with basic aqueous solution made from alkali metal compounds, and especially for lithium, are described in U.S. Pat. No. 4,560,759 the disclosure of which is herein incorporated by reference. Other compounds analogous to the crown ethers and useful for the same purpose are compounds which differ by the replacement of one or more of the oxygen atoms by other kinds of donor atoms, particularly N or S, such as hexamethyl-[14]-4,11-diene$N_4$.

In some embodiments, onium salts include quaternary phosphonium salts and quaternary ammonium salts that may be used as the phase transfer catalyst in the process of the present invention; such compounds can be represented by the following formulas II and III:

$$R^1R^2R^3R^4P^{(+)}X'^{(-)} \quad (II)$$

$$R^1R^2R^3R^4N^{(+)}X'^{(-)} \quad (III)$$

wherein each of $R^1$, $R^2$, $R^3$ and $R^4$, which may be the same or different, is an alkyl group, an aryl group or an aralkyl group, and X' is selected from the group consisting of F, Cl, Br, I, OH, $CO_3$, $HCO_3$, $SO_4$, $HSO_4$, $H_2PO_4$, $HPO_4$ and $PO_4$. Specific examples of these compounds include tetramethylammonium chloride, tetramethylammonium bromide, benzyltriethylammonium chloride, methyltrioctylammonium chloride, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In one embodiment, benzyltriethylammonium chloride is used under strongly basic conditions. Other useful compounds within this class of compounds include those exhibiting high temperature stabilities (e.g., up to about 200° C.) including 4-dialkylaminopyridinium salts, tetraphenylarsonium chloride, bis[tris(dimethylamino)phosphine]iminium chloride, and tetratris[tris(dimethylamino)phosphinimino]phosphonium chloride; the latter two compounds are also reported to be stable in the presence of hot, concentrated sodium hydroxide and, therefore, can be particularly useful.

In some embodiments, polyalkylene glycol ethers are useful as phase transfer catalysts. In some embodiments, the polyalkylene glycol ethers can be represented by the formula:

$$R^6O(R^5O)_tR^7 \quad (IV)$$

wherein $R^5$ is an alkylene group containing two or more carbons, each of $R^6$ and $R^7$, which may be the same or different, is a hydrogen atom, an alkyl group, an aryl group or, an aralkyl group, and t is an integer of at least 2. Such compounds include, for example glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether. Among them, compounds wherein both $R^{-6}$ and $R^{-7}$ are alkyl groups, aryl groups or aralkyl groups are preferred.

In other embodiments, cryptands are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—$OCH_2CH_2$—) groups as in 2.2.2-cryptand (4,7,13,16,21,24-hexaoxa-1,10-diazabicyclo-(8.8.8)hexacosane; available under the brand names Cryptand™ 222 and Kryptofix™ 222). The donor atoms of the bridges may all be O, N, or S, or the compounds may be mixed donor macrocycles in which the bridge strands contain combinations of such donor atoms.

Combinations and mixtures of the above described phase transfer catalysts from within one of the groups may also be useful as well as combinations or mixtures two or more phase transfer catalysts selected from more than one group, for example, crown ethers and oniums, or from more than two of the groups, e.g., quaternary phosphonium salts and quaternary ammonium salts, and crown ethers and polyalkylene glycol ethers.

In some embodiments, the dehydrofluorination process is carried out in batch techniques and in other embodiments, the dehydrofluorination continuous mode of operation. In one embodiment, in the batch mode, the above described components are combined in a suitable vessel for a time sufficient to convert at least a portion of the fluoropropane to hydrofluoroolefin and then the hydrofluoroolefin is recovered from the reaction mixture.

In another embodiment, in a continuous mode of operation, the reaction vessel is charged with the basic aqueous solution, nonaqueous, nonalcoholic solvent, and phase transfer catalyst and the fluoropropane is fed to the reactor. The reaction vessel is fitted with a condenser cooled to a temperature sufficient to reflux the fluoropropane, but permit the hydrofluoroolefin to exit the reaction vessel and collect in an appropriate vessel such as cold trap.

EXAMPLES

The concepts described herein will be further described in the following examples, which do not limit the scope of the invention described in the claims.

Example 1

Example 1 demonstrates the dehydrofluorination of HFC-236ea to HFC-1225ye.

A three neck 2 L flask was equipped with a water ice condenser, thermocouple, and a mechanical stirrer. The condenser exit was connected in series to a $CaSO_4$ drying tube, a molecular sieve drying tube, and a stainless steel trap immersed in dry ice/acetone. A nitrogen-purged bubbler at the exit of the stainless steel trap prevented contamination of the trapped product by moisture.

The flask was charged with water (810 ml), tetrahydrofuran (250 ml), potassium hydroxide pellets (442 g, 56.1 mol), and Aliquat™ 336 (6.74 gm, $1.67 \times 10^{-2}$ mol). The pH of the basic aqueous solution was about 13. Two phases were present in the flask. While vigorously stirring, HFC-236ea was added at a rate of 174 sccm to 291 sccm. About 1080 gm of crude product was collected containing 93.1% Z-1225ye, 1.1% E-1225ye, and 5.4% unreacted HFC-236ea. The 1225ye isomers can be separated from other components in the reaction mixture via any number of separation techniques, including fractional distillation.

Example 2

Example 2 demonstrates the dehydrofluorination of HFC-236ea to HFC-1225ye using an internal standard to check mass balance.

In this reaction, $CHF_2CF_3$ was co-fed with HFC-236ea as an internal standard to measure the instantaneous yield of Z- and E-1225ye. A 500 ml three neck flask was set up as in Example 1. A sample bulb was also installed to measure the concentration of the gas exiting the reactor. The flask was charged with water (200 ml), tetrahydrofuran (60 ml), potassium hydroxide pellets (132 g, 0.0868 mol), and Aliquat™

336 (1.68 gm, 4.17×10⁻³ mol). The pH of the basic aqueous solution was about 13. Two phases were present in the flask.

While stirring at 300-500 rpm, CHF$_2$CF$_3$ (10 sccm) was co-fed with HFC-236ea (91 or 175 sccm) over 6.25 hours. The feed concentration of components and products were analyzed periodically to determine the instantaneous yield of products. After 2.13 hours, the feed composition contained 12 mol % CHF$_2$CF$_3$ and 88 mol % HFC-236ea, while the effluent contained 11 mol % CHF$_2$CF$_3$, 12 mol % HFC-236ea, 76 mol % Z-1225ye, and 1 mol % E-1225ye. The mass balance was high and the single pass yield to Z-1225ye was 86%.

Example 3

Example 3 demonstrates the dehydrofluorination of HFC-245eb to HFC-1234yf.

A three neck 2 L flask was equipped with a water ice condenser, thermocouple, and over-head stirrer. The effluent of the condenser was passed through a CaSO$_4$ drier and then through activated molecular sieves and a stainless steel trap with dip tube immersed in dry ice/acetone. A Krytox® oil bubbler at the exit of the stainless steel trap prevented contamination of the trapped product by moisture.
The flask was charged with water (736 ml), THF (200 ml), KOH pellets (180 g, 3.21 mol), and Aliquat™ 336 (3.13 gm, 7.74×mol). While vigorously stirring, CF$_3$CHFCH$_2$F was added at a rate of about 100 sccm. The pH of the basic aqueous solution was about 13. Two phases were present in the flask. About 247 gm of crude product was collected containing 96.1% 1234yf, 0.5% Z-1234ze, 0.1% E-1234ze and 2.9% unreacted CF$_3$CHFCH$_2$F. Very little exotherm was observed while feeding the CF$_3$CHFCH$_2$F.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges includes each and every value within that range.

What is claimed is:

1. A process for the manufacture of hydrofluoroolefins of the structure CF$_3$CF=CHY, wherein Y can be H or F, comprising reacting at least one fluoropropane reactant of the structure CF$_3$CFXCFY'H, wherein X can be either F or H, and Y' can be either F or H, provided that both X and Y' are not both F, with a basic aqueous solution in the presence of a nonaqueous, nonalcoholic solvent, and in the presence of a phase transfer catalyst wherein the solvent is a ketone or an alkyl or aryl ether and wherein the yield of the reaction is at least 96%.

2. The process of claim 1 wherein the pH of the basic aqueous solution is greater than 8.

3. The process of claim 1 wherein the pH of the basic aqueous solution is between about 10 and about 13.

4. The process of claim 1 wherein the basic aqueous solution is made from a base selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

5. The process of claim 1 wherein the phase transfer is catalyst is selected from the group consisting of crown ethers, onium salts, cryptands, polyalkylene glycols, and mixtures thereof.

6. The process of claim 1 wherein Y is F, X is F, and Y' is H, or wherein Y is F, X is H, and Y' is F, or wherein Y is H, X is H and Y' is H.

7. The process of claim 5 wherein the phase transfer catalyst is either 18-crown-6, 15-crown-5, a quaternary ammonium salt or mixtures thereof.

8. The process of claim 7 wherein the base in the basic aqueous solution is potassium hydroxide and the phase transfer catalyst is either 18-crown-6, methyltrioctylammonium chloride or mixtures thereof.

9. The process of claim 1 wherein the dehydrofluorination is conducted at a temperature of from about 20° C. to about 150° C.

10. The process of claim 1 wherein the nonaqueous, nonalcoholic solvent is selected from the group consisting of 2-methyltetrahydrofuran, tetrahydrofuran, dioxane, diglyme, tetraglyme and mixtures thereof.

11. The process of claim 1 wherein the molar ratio of base in the basic aqueous solution to fluoropropane is from about 0.75:1 to about 10:1.

12. The process of claim 1 wherein the molar ratio of base to fluoropropane is from about 1:1 to about 4:1.

13. A composition comprising a hydrofluoroolefin of the structure CF$_3$CF=CHY, wherein Y can be H or F, produced by the process comprising reacting at least one fluoropropane reactant of the structure CF$_3$CFXCFY'H, wherein X can be either F or H, and Y' can be either F or H, provided that both X and Y' are not both F, with a basic aqueous solution in a nonaqueous, nonalcoholic solvent, and in the presence of a phase transfer catalyst ether and wherein the yield of the reaction is at least 96%.

14. The composition of claim 13 wherein the base in basic aqueous solution is selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

* * * * *